(12) United States Patent
Thornton et al.

(10) Patent No.: US 10,022,107 B2
(45) Date of Patent: Jul. 17, 2018

(54) METHOD AND SYSTEM FOR CORRECTING FAT-INDUCED ABERRATIONS (71) Applicant: ENDRA Life Sciences Inc., Ann Arbor, MI (US)

(72) Inventors: Michael M. Thornton, London (CA); Kai Thomenius, Clifton Park, NY (US); Aghapi Mordovanakis, Ann Arbor, MI (US)

(73) Assignee: ENDRA Life Sciences Inc., Ann Arbor, MI (US)

( * ) Notice: Subject to any disclaimer, the term of this patent is extended or adjusted under 35 U.S.C. 154(b) by 0 days.

(21) Appl. No.: 15/223,607

(22) Filed: Jul. 29, 2016

(65) Prior Publication Data

US 2017/0032519 A1 Feb. 2, 2017

Related U.S. Application Data

(60) Provisional application No. 62/199,355, filed on Jul. 31, 2015.

(51) Int. Cl.
*G06T 7/00* (2017.01)
*A61B 8/08* (2006.01)
*G01S 7/52* (2006.01)
*G06T 7/11* (2017.01)

(52) U.S. Cl.
CPC .......... *A61B 8/5223* (2013.01); *A61B 8/5269* (2013.01); *G01S 7/52049* (2013.01); *G06T 7/11* (2017.01); *G06T 2207/10132* (2013.01); *G06T 2207/30004* (2013.01)

(58) Field of Classification Search
None
See application file for complete search history.

(56) References Cited

U.S. PATENT DOCUMENTS

| 2005/0027188 | A1* | 2/2005 | Metaxas | A61B 5/055 600/410 |
| 2011/0040176 | A1* | 2/2011 | Razansky | A61B 5/0095 600/425 |
| 2013/0190595 | A1* | 7/2013 | Oraevsky | A61B 5/0095 600/407 |
| 2017/0122915 | A1* | 5/2017 | Vogt | C08K 5/12 |

FOREIGN PATENT DOCUMENTS

WO    WO 2015013196 A2 *    1/2015    ......... G01S 7/52046

* cited by examiner

*Primary Examiner* — Vu Le
*Assistant Examiner* — Tracy Mangialaschi
(74) *Attorney, Agent, or Firm* — Tarolli, Sundheim, Covell & Tummino LLP (57) ABSTRACT

A method for correcting fat-induced aberrations in ultrasound imaging comprises segmenting a thermoacoustic absorption image of a region of interest into at least one fat region and at least one non-fat region, creating a speed of sound map by assigning a speed of sound to each region based on tissue type of the region, correcting aberrations in the segmented thermoacoustic absorption image using the assigned speeds of sound thereby generating a corrected thermoacoustic image, and correcting an ultrasound image of the region of interest using the corrected thermoacoustic image and the speed of sound map.

23 Claims, 4 Drawing Sheets

METHOD AND SYSTEM FOR CORRECTING FAT-INDUCED ABERRATIONS

CROSS-REFERENCE TO RELATED APPLICATIONS

This application claims the benefit of U.S. Provisional Patent Application No. 62/199,355 entitled "System and Methods for Reducing Errors Due to Fat-Induced Aberrations in Ultrasound," filed on Jul. 31, 2015, the content of which is incorporated herein by reference in its entirety.

FIELD

This application relates to a method and system for correcting fat-induced aberrations in ultrasound imaging.

BACKGROUND

Ultrasound imaging uses sound waves with frequencies higher than those audible to humans (>20 000 Hz). These sound waves are pulsed into tissue using a probe. The sound waves echo off the tissue, with different tissues reflecting varying degrees of sound. These echoes are analyzed through signal processing and are further processed using clinical ultrasound reconstruction algorithms to reconstruct ultrasound images for presentation and interpretation by an operator. Many different types of images can be reconstructed using ultrasound imaging. One such type is a B-mode image which displays the acoustic impedance of a two-dimensional cross-section of tissue.

Ultrasound imaging reconstruction requires knowledge of the speed of sound in the imaged medium. Although the speed of sound in soft tissues ranges from 1450 m/s in fat to 1590 m/s in the liver, clinical ultrasound reconstruction algorithms assume a homogenous speed of sound of 1540 m/s which is a weighted average for a model human. Spatial variation of the speed of sound within a region of interest of the imaged medium and the discrepancies between assumed values and actual values result in phase and refractive errors or aberrations incurred for both the transmitted sound waves and the reflected echoes. These aberrations contribute to contrast and resolution loss in reconstructed images as well as introduce distortions, artifacts and errors in feature localization.

Figure 1:
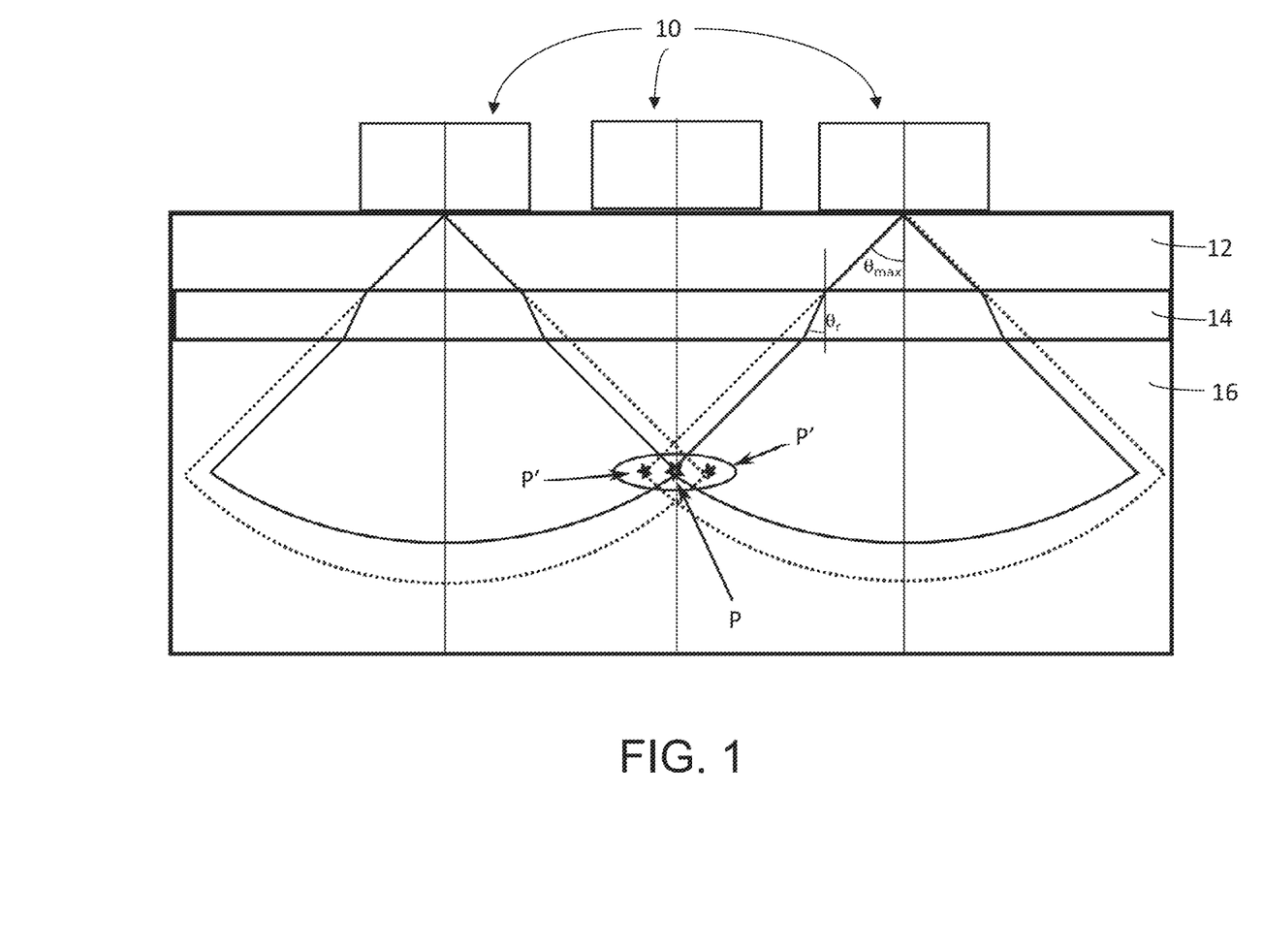
FIG. 1 is a schematic view of a prior art ultrasound imaging system.

An exemplary ultrasound imaging system is shown in FIG. 1. As can be seen, the ultrasound imaging system comprises ultrasound transducer arrays 10 that emit sound waves into a region of interest (ROI), in this case tissue comprising non-fat regions 12 and 16 and fat region 14. As the sound waves travel from the non-fat region 12 to the fat region 14 to the non-fat region 16, the sound waves are refracted by an angle of $\theta_r$. As a result, the position P of a structure within the region of interest ROI appears at shifted positions P'. The discrepancy between the actual position and the apparent position of the structure may be as high as several millimeters and significantly affects the resolution of the ultrasound image. If the thickness of fat region 14 is known, the shift in the position of the structure can be corrected. However, in obese patients, the thickness of the fat region can vary considerably resulting in blurred images.

A number of methods and techniques have been developed to correct for fat-induced aberrations in ultrasound imaging due to a spatially-varying speed of sound. In some common methods, algorithms are used that infer the average ultrasound phase distortion along a given direction by analyzing the arrival phase variations from known guide stars or beacons. These methods are however, computationally intensive, require a number of iterations and are not always accurate.

In other common methods, clinical information obtained using various imaging modalities, such as for example ultrasound imaging, X-ray computed tomography or magnetic resonance imaging, is relied upon to determine the boundaries and thickness of fat layers. Instead of using a homogenous speed of sound, these methods use two or more values to represent the speed of sound within each layer. These methods require access to expensive imaging modalities and are limited by their capability to delineate the boundaries of fat layers in obese patients.

Still other methods have been employed. For example, U.S. Pat. No. 6,705,994 to Vortman et al. discloses a method of imaging a site of interest in a body using an ultrasound probe comprising a plurality of ultrasound transducer elements. The method comprises obtaining an ultrasound image of a pass zone between the ultrasound probe and the site of interest. The image includes the site of interest and a plurality of tissue regions in the pass zone between the site of interest and the ultrasound probe. Boundaries of a selected tissue region in the pass zone are determined from the image. Focusing delay times are then computed for each ultrasound transducer element based in part on the speed of sound in the selected tissue region other than an average speed of sound in body tissue, and the boundaries of the selected tissue region. A speed of sound in the selected tissue region is used. In embodiments, refraction is considered. Ultrasound imaging of the site of interest is conducted employing the computed delay times. Fat and bone tissue regions are selected if present. Other tissue regions may be selected, as well. The boundaries of the tissue region or regions may be determined by segmentation. Tissue inhomogeneity is thereby compensated for, improving image contrast resolution.

As another example, U.S. Pat. No. 8,784,318 to Napolitano et al. discloses an ultrasound scanner equipped with an image data processing unit that can perform adaptive parameter optimization during image formation and processing. In an embodiment, an ultrasound system comprises a channel data memory to store channel data obtained by digitizing ultrasound image data produced by an image scan, an image data processor configured to process the stored channel data in the memory to reconstruct an ultrasound image for each of a plurality of trial values of at least one parameter to be optimized, and a parameter optimization unit configured to evaluate an image quality of the reconstructed ultrasound image for each trial value of the at least one parameter, and to determine the optimized value of the at least one parameter based on the evaluated image quality.

Although techniques for correcting for fat-induced aberrations in ultrasound imaging have been considered, improvements are desired. It is therefore an object at least to provide a novel method and system for correcting fat-induced aberrations in ultrasound imaging.

SUMMARY

Accordingly, in one aspect there is provided a method for correcting fat-induced aberrations in ultrasound imaging, the method comprising segmenting a thermoacoustic absorption image of a region of interest into at least one fat region and at least one non-fat region, creating a speed of sound map by assigning a speed of sound to each region based on tissue type of the region, correcting aberrations in the segmented thermoacoustic absorption image using the assigned speeds of sound thereby generating a corrected thermoacoustic image, and correcting an ultrasound image of the region of interest using the corrected thermoacoustic image and the speed of sound map.

In an embodiment, the method further comprises obtaining thermoacoustic image data of a region of interest and reconstructing the thermoacoustic absorption image using the thermoacoustic image data. The method further comprises obtaining ultrasound image data of the region of interest and reconstructing the ultrasound image using the ultrasound image data.

In an embodiment, the segmenting further comprises determining a threshold intensity value, classifying pixels within the thermoacoustic absorption image having a threshold above the threshold intensity as being part of the at least one non-fat region; and classifying pixels within the thermoacoustic absorption image having a threshold below the threshold intensity as being part of the at least one fat region.

According to another aspect there is provided a system comprising a thermoacoustic imaging system configured to capture a thermoacoustic image of a region of interest, an ultrasound imaging system configured to capture an ultrasound image of the region of interest, and a processing unit communicatively coupled to the thermoacoustic imaging system and the ultrasound imaging system, the processing unit configured to process thermoacoustic image data received from the thermoacoustic imaging system to generate a thermoacoustic absorption image of the region of interest, segment the thermoacoustic absorption image into at least one fat region and at least one non-fat region, create a speed of sound map by assigning a speed of sound to each region based on tissue type of the region, correct aberrations in the segmented thermoacoustic absorption image using the assigned speeds of sound thereby generating a corrected thermoacoustic image; and correct the ultrasound image captured by the ultrasound imaging system of the region of interest using the corrected thermoacoustic image and the speed of sound map.

According to another aspect, there is provided a non-transitory computer-readable medium having stored thereon a computer program comprising computer program code executable by a computer to perform a method comprising segmenting a thermoacoustic absorption image of a region of interest into at least one fat region and at least one non-fat region, creating a speed of sound map by assigning a speed of sound to each region based on tissue type of the region, correcting aberrations in the segmented thermoacoustic absorption image using the assigned speeds of sound thereby generating a corrected thermoacoustic image, and correcting an ultrasound image of the region of interest using the corrected thermoacoustic image and the speed of sound map.

According to another aspect there is provided a system comprising a thermoacoustic imaging system, an ultrasound imaging system, and a processing unit configured to process thermoacoustic image data received from the thermoacoustic imaging system to generate a thermoacoustic absorption image, to identify at least one fat region and at least one non-fat region within the thermoacoustic absorption image, to generate a speed of sound map for the fat and non-fat regions and to generate a corrected thermoacoustic absorption image, and process ultrasound image data received from the ultrasound imaging system using the speed of sound map and the corrected thermoacoustic absorption image to generate a corrected ultrasound image.

According to another aspect there is provided a method for correcting fat-induced aberrations in ultrasound imaging, the method comprising segmenting a thermoacoustic absorption image into at least one fat region and at least one non-fat region, creating a speed of sound map by assigning a speed of sound to each region based on tissue type of the region, correcting aberrations in the segmented thermoacoustic absorption image using the speed of sound map thereby generating a corrected thermoacoustic image, and adjusting parameters of an ultrasound imaging system using the corrected thermoacoustic image and the speed of sound map to correct for fat-induced aberrations.

BRIEF DESCRIPTION OF THE DRAWINGS

Embodiments will now be described more fully with reference to the accompanying drawings in which.

DETAILED DESCRIPTION OF THE EMBODIMENTS

In the following, a method and system for correcting fat-induced aberrations in ultrasound imaging will be described. The method comprises segmenting a thermoacoustic absorption image into at least one fat region and at least one non-fat region, creating a speed of sound map by assigning a speed of sound to each region based on tissue type of the region, correcting aberrations in the segmented image using the assigned speeds of sound thereby generating a corrected thermoacoustic image, and correcting an ultrasound image of the region of interest using the corrected thermoacoustic image. Thermoacoustic imaging is utilized to obtain a thermoacoustic image of a region of interest where a high-resolution ultrasound image is desired. During segmentation, the thermoacoustic image is analyzed to determine the thickness and boundaries of fat layers within the region of interest in order to correct for phase and refractive errors in the ultrasound image due to the variation in speed of sound in these regions. The thermoacoustic image therefore is used to reduce fat-induced aberrations in the ultrasound image to enhance its contrast and resolution.

Figure 2:
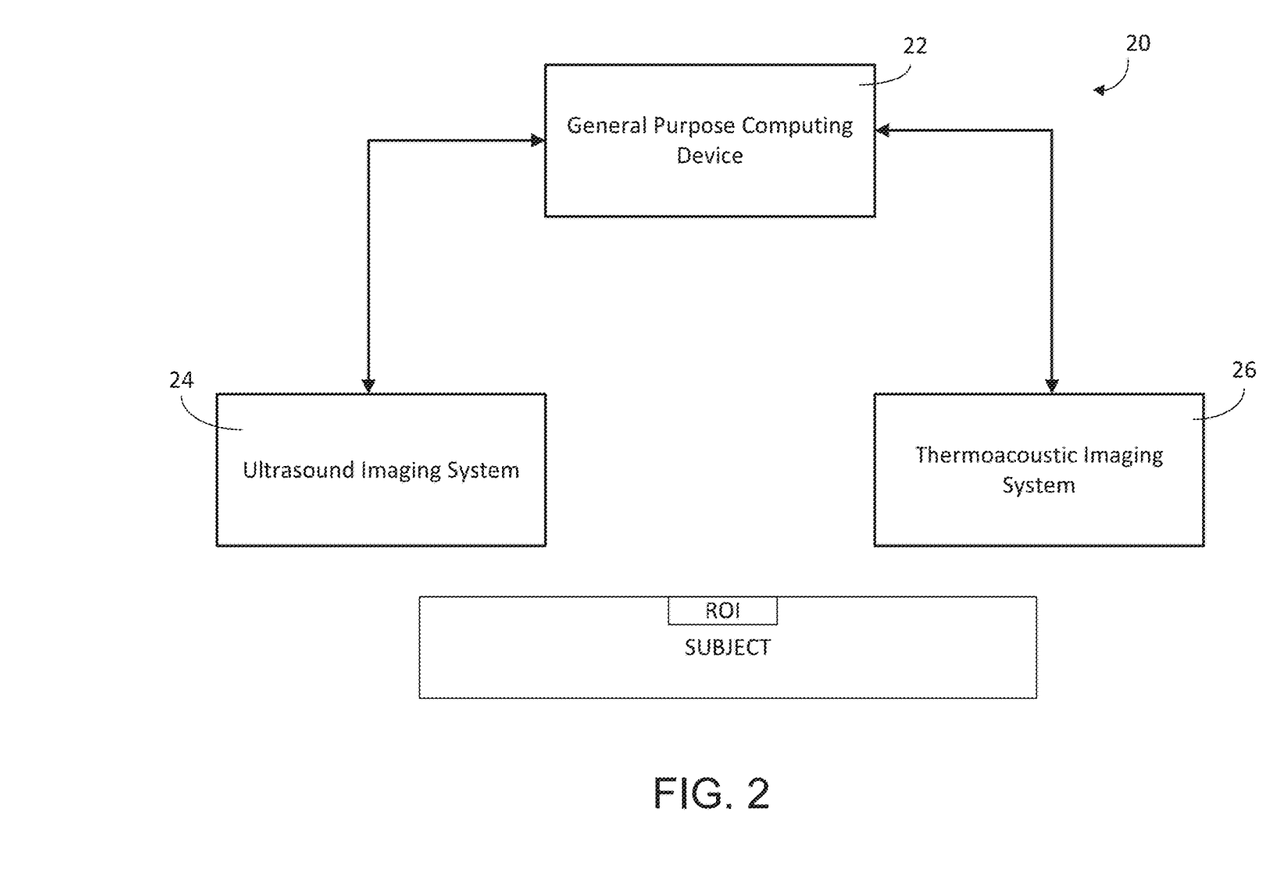
FIG. 2 is a schematic view of an imaging system in accordance with the subject application.

Turning now to FIG. 2, an imaging system is shown and is generally identified by reference numeral 20. As can be seen, the imaging system 20 comprises a general purpose computing device 22 communicatively coupled to an ultrasound imaging system 24 and a thermoacoustic imaging system 26. The ultrasound imaging system 24 and thermoacoustic imaging system 26 are configured to obtain ultrasound image data and thermoacoustic image data, respectively, of a region of interest ROI associated with a subject.

The general purpose computing device 22 in this embodiment is a personal computer or other suitable processing device comprising, for example, a processing unit comprising one or more processors, system memory (volatile and/or non-volatile memory), other non-removable or removable memory (e.g., a hard disk drive, RAM, ROM, EEPROM, CD-ROM, DVD, flash memory, etc.) and a system bus coupling the various computer components to the processing unit. The general purpose computing device 22 may also comprise networking capabilities using Ethernet, Wi-Fi, and/or other suitable network format, to enable connection to shared or remote drives, one or more networked computers, or other networked devices. One or more input devices, such as a mouse and a keyboard (not shown) are coupled to the general purpose computing device 22 for receiving user input. A display device (not shown), such as a computer screen or monitor, is coupled to the general purpose computer device 22 for displaying one or more generated images that are based on ultrasound image data received from the ultrasound imaging system 24 and/or the thermoacoustic image data received from thermoacoustic imaging system 26.

The ultrasound imaging system 24 comprises one or more ultrasound transducer arrays (not shown) configured to emit sound waves into the region of interest ROI of the subject. In this embodiment, the one or more ultrasound transducer arrays are disconnectable from the ultrasound imaging system 24. The sound waves directed into the region of interest ROI of the subject echo off tissue within the region of interest ROI, with different tissues reflecting varying degrees of sound. These echoes are received by the one or more ultrasound transducer arrays and are processed by the ultrasound imaging system 24 before being communicated as ultrasound image data to the general purpose computing device 22 for further processing and for presentation and interpretation by an operator. As ultrasound imaging systems are known in the art, further specifics of the ultrasound imaging system 24 will not be described further herein.

The thermoacoustic imaging system 26 comprises a radio-frequency (RF) source (not shown) configured to generate short pulses of RF electromagnetic radiation that are directed into the region of interest ROI of the subject to deliver energy to tissue within the region of interest ROI of the subject, which in turn induces acoustic pressure waves that are detected using one or more ultrasound transducer arrays (not shown). In this embodiment, the thermoacoustic imaging system 26 makes use of the one or more ultrasound transducer arrays of the ultrasound imaging system 26 by disconnecting the one or more ultrasound transducer arrays of the ultrasound imaging system 24 and connecting them to the thermoacoustic imaging system 26 and as such, coordinate mapping between transducer arrays is not required as will be described. In this embodiment, the RF source has a frequency between about 10 Mhz and 100 Ghz and has a pulse duration between about 0.1 nanoseconds and 10 microseconds. Acoustic pressure waves detected by the one or more ultrasound transducer arrays are processed and communicated as thermoacoustic image data to the general purpose computing device 22 for further processing and for presentation and interpretation by an operator. As thermoacoustic imaging systems are known in the art, further specifics of the thermoacoustic imaging system 26 will not be described further herein.

Figure 3:
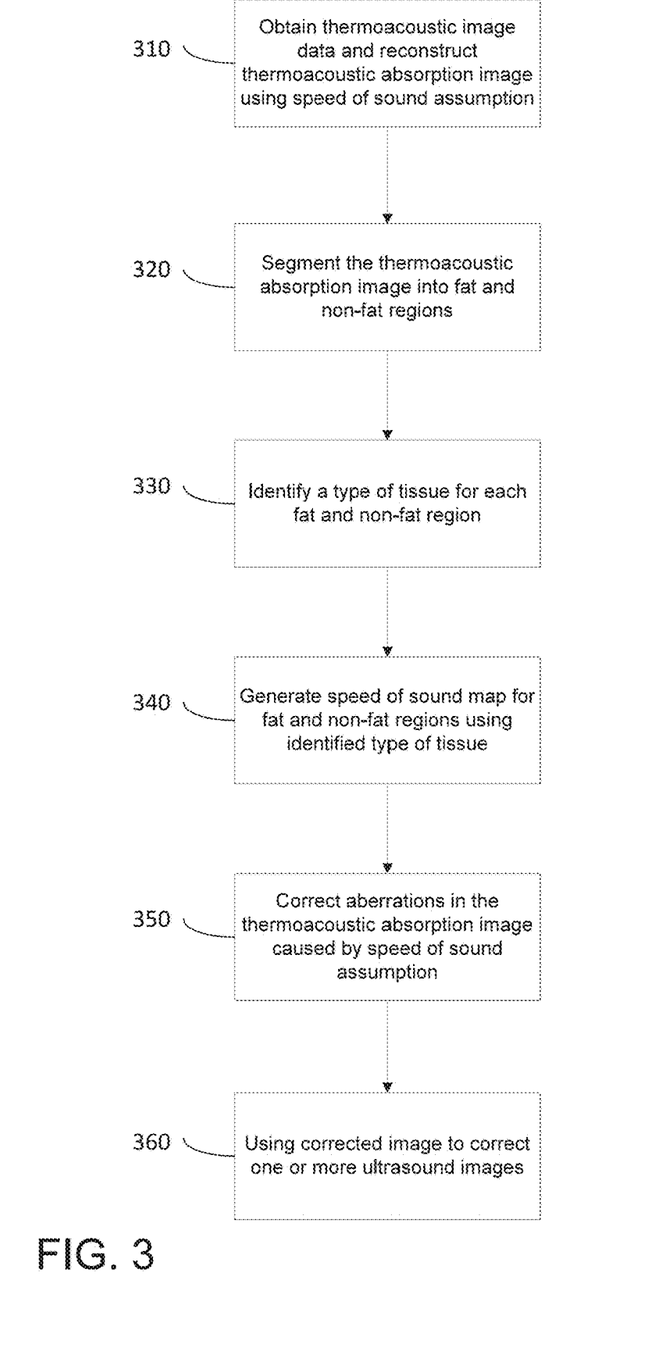
FIG. 3 is a flowchart showing a method of correcting fat-induced aberrations in ultrasound images.
Figure 4A:
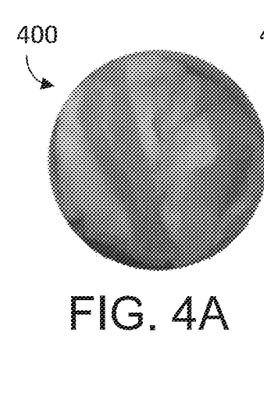
FIG. 4A is an image of a region of interest.
Figure 4B:
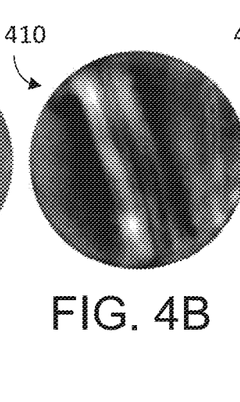
FIG. 4B is a thermoacoustic absorption image of the region of interest shown in FIG. 4A.

Operation of the imaging system 20 will now be described with reference to FIGS. 2, 3 and 4A to 4C. During operation of the imaging system 20, the RF source of the thermoacoustic imaging system 26 is conditioned to deliver energy to tissue within the region of interest ROI of the subject in the form of short pulses of RF electromagnetic radiation, which in turn induces acoustic pressure waves that are detected by the one or more ultrasound transducer arrays. An exemplary region of interest ROI is shown in FIG. 4A and is generally identified by reference numeral 400. The acoustic pressure waves detected by the one or more ultrasound transducer arrays are processed by the thermoacoustic imaging system 26 to yield thermoacoustic image data associated with the region of interest ROI of the subject. The thermoacoustic image data associated with the region of interest ROI is then communicated to the general purpose computing device 22. The general purpose computing device 22 in turn processes the thermoacoustic image data to reconstruct a thermoacoustic absorption image of the region of interest ROI (step 310). In this embodiment, the thermoacoustic absorption image is reconstructed using an assumed speed of sound of 1540 m/s and using methods such as that disclosed in "Photoacoustic Imaging with Deconvolution Algorithm," Physics in Medicine and Biology, 49, 3117-3127 authored by Wang et al., 2004, the relevant portions of which are incorporated herein by reference. Generally, the thermoacoustic absorption image is reconstructed by calculating a convolution relationship between photoacoustic signals measured by the one or more ultrasound transducer arrays and optical absorption distribution. The projection of the optical absorption distribution is obtained by deconvolving a recorded photoacoustic signal originating from a point source. A modified filtered back projection algorithm is used to reconstruct the optical absorption distribution. An exemplary thermoacoustic absorption image of the region of interest ROI is shown in FIG. 4B and is generally identified by reference numeral 410.

Figure 4C:
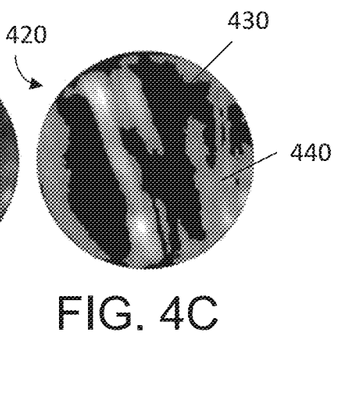
FIG. 4C is a segmented thermoacoustic absorption image of the region of interest shown in FIG. 4A.

The thermoacoustic absorption image of the region of interest ROI is then segmented by the general purpose computing device 22 into fat regions and non-fat regions based on the intensity of pixels within the thermoacoustic absorption image (step 320). In this embodiment, the thermoacoustic absorption image is segmented using an intensity-based threshold wherein pixels having a thermoacoustic intensity above the threshold are classified as being non-fat and pixels having a thermoacoustic intensity less than or equal to the threshold are classified as being fat. Groups of pixels classified as being non-fat are thus associated with a non-fat region and groups of pixels classified as being fat are thus associated with a fat region. An exemplary segmented thermoacoustic absorption image 420 based on the thermoacoustic absorption image 410 of FIG. 4B is shown in FIG. 4C. As can be seen in FIG. 4C, the segmented thermoacoustic absorption image 420 comprises fat regions 430 and non-fat regions 440. The fat regions 430 appear dark and the non-fat regions 440 appear significantly lighter than the fat regions 430.

A type of tissue is identified for each of the fat and non-fat regions (step 330). In this embodiment, the average intensity of the pixels within each particular region is calculated to identify the type of tissue within that particular region. In the example shown in FIG. 4C, the fat regions 430 are identified as fat and the non-fat regions 440 are identified as muscle.

A speed of sound is then assigned to each of the fat and non-fat regions based on the identified tissue type and a speed of sound map is created (step 340). In this embodiment, the speed of sound map is generated using known values for the speed of sound through various types of tissues. The data used for this embodiment is disclosed in "Physical Properties of Tissues: A Complete Reference Book," Academic Press authored by Duck et al., 1990, the relevant portions of which are incorporated herein by reference. Generally, the data used is shown in Table 1 below:

TABLE 1

Speed of Sound of Various Tissues or Materials

| Tissue or Material | Density (g/cm³) | Speed of Sound (m/s) | Acoustic Impedance (kg/(sec · m²) × 10⁶) |
|---|---|---|---|
| Water | 1 | 1480 | 1.48 |
| Blood | 1.055 | 1575 | 1.66 |
| Fat | 0.95 | 1450 | 1.38 |
| Liver | 1.06 | 1590 | 1.69 |
| Kidney | 1.05 | 1570 | 1.65 |
| Brain | 1.03 | 1550 | 1.60 |
| Heart | 1.045 | 1570 | 1.64 |
| Muscle (along the fibers) | 1.065 | 1575 | 1.68 |
| Muscle (across the fibers) | 1.065 | 1590 | 1.69 |
| Skin | 1.15 | 1730 | 1.99 |
| Eye (lens) | 1.04 | 1650 | 1.72 |
| Eye (vitreous humor) | 1.01 | 1525 | 1.54 |
| Bone axial (longitudinal waves) | 1.9 | 4080 | 7.75 |
| Bone axial (shear waves) | 1.9 | 2800 | 5.32 |
| Teeth (dentine) | 2.2 | 3600 | 7.92 |
| Teeth (enamel) | 2.9 | 5500 | 15.95 |

Using Table 1 and the segmented thermoacoustic absorption image 420 shown in FIG. 4C, the fat regions 430 are assigned a speed of sound of 1450 m/s. The non-fat regions 440 are assigned a speed of sound calculated using a weighted average of various tissue types of Table 1 which is equal to 1540 m/s.

Since the thermoacoustic absorption image that is segmented in step 320 was reconstructed in step 310 using a single speed of sound assumption, aberrations appear within the segmented thermoacoustic absorption image. Aberrations in the segmented thermoacoustic absorption image are corrected using the speed of sound map (step 350). In this embodiment, the aberrations are corrected for each fat and non-fat region. Within each fat and non-fat region, pixels are scaled along a direction of ultrasound propagation by a ratio of the speed of sound assigned during step 340 to the assumed speed of sound used during step 310. Specifically, the pixels within the fat regions 430 are scaled by a ratio of 1450 m/s to 1540 m/s. Since the pixels within the non-fat regions 440 are assigned a speed of sound of 1540 m/s which is equal to the assumed speed of sound, these pixels are not scaled. As a result, an aberration-corrected segmented thermoacoustic absorption image delineating boundaries between the fat regions 430 and the non-fat regions 440 is generated.

The aberration-corrected segmented thermoacoustic absorption image and the associated speed of sound map are then used to correct one or more ultrasound images of the region of interest (step 360). As mentioned above, in this embodiment, the one or more ultrasound transducer arrays used by the thermoacoustic imaging system 26 are also used by the ultrasound imaging system 24. As such, both the ultrasound image and the aberration-corrected segmented thermoacoustic absorption image are defined with respect to the same coordinate system. As a result, registering the coordinate frames of the aberration-corrected segmented thermoacoustic absorption image and ultrasound image is not required. The aberration-corrected segmented thermoacoustic absorption image generated during step 350 and the speed of sound map generated during step 340 are used with one or more image correction algorithms to obtain, reconstruct and correct an ultrasound image using one or more correction algorithms. Exemplary correction algorithms are disclosed in "Sound Speed Correction in Ultrasound Imaging," ScienceDirect, authored by Napolitano et al., Jul. 20, 2006 and "Refraction Correction in 3D Transcranial Ultrasound Imaging," Ultrason Imaging, authored by Lindsey et al., May 12, 2014, the relevant portions of which are incorporated herein by reference.

Although in embodiments above the aberration-corrected segmented thermoacoustic absorption image and the speed of sound map are used with one or more image correction algorithms to correct an ultrasound image, those skilled in the art will appreciate that the aberration-corrected segmented thermoacoustic absorption image and the speed of sound map may be used to adjust parameters of the ultrasound imaging system prior to imaging. For example, in embodiments one or more image correction algorithms may be used to adjust the relative phases of the one or more ultrasound transducer arrays during beamforming to correct for phase delays that may destroy the emitted ultrasound beam and/or correct for phase delays in the return beam to produce an aberration-corrected ultrasound image. In addition, the corrected segmented thermoacoustic absorption image and the speed of sound map may be used to correct for refractive artifacts, resulting from the refraction of ultrasound waves at the boundaries between the fat and non-fat regions for the transmitted ultrasound beam, the reflected ultrasound echoes, or both.

Although in embodiments above the one or more ultrasound transducer arrays are described as being disconnectable from the ultrasound imaging system 24 and reconnectable to the thermoacoustic imaging system 26, those skilled in the art will appreciate that alternatives are possible. For example, the ultrasound imaging system 24 and the thermoacoustic imaging system 26 may have their own respective one or more transducer arrays. In this case, it is preferred that one or more ultrasound transducer arrays of the ultrasound and thermoacoustic imaging systems be of the same type or model. In this embodiment, it will be appreciated that during processing the coordinate frames of the aberration-corrected segmented thermoacoustic absorption image and ultrasound images are registered before the aberration-corrected segmented thermoacoustic absorption image is used to correct the one or more ultrasound images at step 360. In this embodiment, the registering comprises mapping coordinates of the aberration-corrected segmented thermoacoustic absorption image to coordinates of the ultrasound image. In another embodiment, the one or more ultrasound transducer arrays may be connected to a hub which itself is connected to the ultrasound imaging system and the thermoacoustic imaging system. In this embodiment, the hub may be controlled by the general purpose computing device 22 or by other input to switch operation between the ultrasound imaging system and the thermoacoustic imaging system and vice versa.

In another embodiment, different types or models of transducer arrays may be used with the thermoacoustic and ultrasound imaging systems. In this embodiment, a transform is used to map the aberration-corrected segmented thermoacoustic absorption image to the ultrasound image. In another embodiment, in the event that knowledge of transducer array geometry is not readily available, the aberration-corrected segmented thermoacoustic absorption image may be mapped to the ultrasound image using phantom reference points. In this embodiment, a transform may be used to map known phantom reference points from the aberration-corrected segmented thermoacoustic absorption image to the phantom reference points on the ultrasound image.

Although in embodiments above the thermoacoustic absorption image is segmented into fat regions and non-fat regions using an intensity-based threshold wherein pixels having an intensity above the threshold are classified as being non-fat and pixels having an intensity less than or equal to the threshold are classified as being fat, those skilled in the art will appreciate that alternatives are available. For example, in another embodiment the thermoacoustic absorption image may be presented on the display device of the general purpose computing device 22 for viewing by an operator. In this embodiment, the operator may be able to manually select fat and non-fat regions using an input device based on an intensity threshold. In this embodiment, a graphic may be displayed on the display device indicating the intensity threshold to the operator.

In another embodiment, the intensity threshold may be determined by an algorithm based on a known ratio of thermoacoustic signal magnitude for both fat and lean tissue. In this embodiment, if the ratio of the thermoacoustic signal magnitude of lean tissue to that of fat is R for a given radio frequency (RD), then the segmentation threshold may be determined. A homogenous region of lean tissue within the thermoacoustic absorption image is selected and the mean $\mu_{lean}$ and standard deviation a of the signal in the homogenous region of lean tissue are calculated. Then, the segmentation threshold may be calculated using equation 1:

$$\text{Threshold} = \mu_{lean}(1+2\sigma)/R \qquad (1)$$

In other embodiments, algorithms such as for example morphological transforms or histogram equalization may be used to enhance the contrast of the thermoacoustic absorption image prior to segmentation.

As will be appreciated, embodiments of image processing described above can be performed on ultrasound and thermoacoustic images in real-time or off-line using images stored in memory.

Although the thermoacoustic imaging system is described as comprising an RF source configured to generate short pulses of RF electromagnetic radiation, those skilled in the art will appreciate that in other embodiments the thermoacoustic imaging system may comprise a visible light source or an infrared radiation source with a wavelength between 400 nm and 10 μm and a pulse duration between 10 picoseconds and 10 microseconds.

Those skilled in the art will appreciate that the corrected segmented thermoacoustic absorption image and speed of sound map may be used to correct ultrasound images which are two-dimensional (B-mode ultrasound imaging). Other imaging technologies may also be employed such as for example A-mode ultrasound imaging, C-mode ultrasound imaging, M-mode ultrasound imaging, Doppler imaging and shear-wave elastography.

Embodiments described above may also be used with imaging systems where images are acquired in a time sequence, to construct a time evolution representation of a volume or region of interest.

Embodiments described above may also be used with various therapy treatments such as for example high intensity focused ultrasound (HIFU) and histotripsy. Embodiments described above may be used to pre-compensate the phase of ultrasound waves for each transducer in a transducer array during beamforming of a high-intensity focused ultrasound beam. Embodiments described above may guide or monitor these therapies to ensure that the intended therapy volume is exposed and treated.

Although in embodiments described above the thermoacoustic imaging system and the ultrasound imaging system are described as using one or more ultrasound transducer arrays, those skilled in the art will appreciate that the alternatives are available. For example, a single transducer element, an ultrasound transducer array having a linear or curved one-dimensional array, or a two-dimensional ultrasound transducer array may be used. In addition, a gel-like material or water capsule may be used to interface the one or more ultrasound transducer arrays with the region of interest.

Those skilled in the art will appreciate that the region of interest may encompass one or more objects such as for example the heart, kidney(s), lung, esophagus, thymus, breast, prostate, brain, muscle, nervous tissue, epithelial tissue, bladder, gallbladder, intestine, liver, pancreas, spleen, stomach, testes, ovaries, uterus, skin and adipose tissues.

Those skilled in the art will appreciate that the above-described ultrasound images and thermoacoustic images may be two-dimensional or three-dimensional.

Although the thermoacoustic absorption image is described as being reconstructed using methods disclosed by Wang et al, those skilled in the art will appreciate that any known method for reconstructing a thermoacoustic absorption image may be used.

Although embodiments have been described above with reference to the accompanying drawings, those of skill in the art will appreciate that variations and modifications may be made without departing from the scope thereof as defined by the appended claims.

What is claimed is:

1. A method for correcting fat-induced aberrations in ultrasound imaging, the method comprising:
    reconstructing a thermoacoustic absorption image of a region of interest using an assumed speed of sound value;
    segmenting the thermoacoustic absorption image into at least one region containing fatty tissue and at least one region containing lean tissue;
    creating a speed of sound map by assigning a speed of sound value to each region, the assigned speed of sound value being dependent on an amount of fatty tissue within that region;
    correcting aberrations for each region in the segmented thermoacoustic absorption image using a ratio of the assigned speed of sound value to the assumed speed of sound value, thereby generating a corrected thermoacoustic image; and
    correcting an ultrasound image of the region of interest using the corrected thermoacoustic image and the speed of sound map.

2. The method of claim 1 further comprising:
    obtaining thermoacoustic image data of the region of interest; and
    reconstructing the thermoacoustic absorption image using the thermoacoustic image data.

3. The method of claim 2 further comprising:
    obtaining ultrasound image data of the region of interest and reconstructing the ultrasound image using the ultrasound image data.

4. The method of claim 1 wherein the segmenting comprises:
    determining a threshold intensity value;
    classifying pixels within the thermoacoustic absorption image having a threshold above the threshold intensity as being part of the at least one region containing lean tissue; and classifying pixels within the thermoacoustic absorption image having a threshold below the threshold intensity as being part of the at least one region containing fatty tissue.

5. The method of claim 4 wherein determining the threshold intensity value comprises calculating the threshold intensity value using a mean intensity value and a standard deviation of the intensity value.

6. The method of claim 1 wherein the segmenting comprises:
receiving user input via an input device coupled to a processing structure identifying the at least one region containing fatty tissue and the at least one region containing lean tissue.

7. The method of claim 1 wherein assigning the speed of sound value to each region comprises looking up the speed of sound value in a lookup table.

8. The method of claim 1 further comprising registering coordinate frames of the corrected thermoacoustic image and the ultrasound image.

9. The method of claim 8 wherein the registering comprises mapping coordinates of the corrected thermoacoustic image with coordinates of the ultrasound image.

10. A system comprising:
a thermoacoustic imaging system configured to capture a thermoacoustic image of a region of interest;
an ultrasound imaging system configured to capture an ultrasound image of the region of interest; and
a processing unit communicatively coupled to the thermoacoustic imaging system and the ultrasound imaging system, the processing unit configured to:
process thermoacoustic image data received from the thermoacoustic imaging system to generate a thermoacoustic absorption image of the region of interest using an assumed speed of sound value;
segment the thermoacoustic absorption image into at least one region containing fatty tissue and at least one region containing lean tissue;
create a speed of sound map by assigning a speed of sound value to each region, the assigned speed of sound value being dependent on an amount of fatty tissue within that region;
correct aberrations for each region in the segmented thermoacoustic absorption image using a ratio of the assigned speed of sound value to the assumed speed of sound value thereby generating a corrected thermoacoustic image; and
correct the ultrasound image captured by the ultrasound imaging system of the region of interest using the corrected thermoacoustic image and the speed of sound map.

11. The system of claim 10 wherein during the segmenting, the processing unit is configured to:
determine a threshold intensity value;
classify pixels within the thermoacoustic absorption image having a threshold above the threshold intensity as being part of the at least one region containing lean tissue; and
classify pixels within the thermoacoustic absorption image having a threshold below the threshold intensity as being part of the at least one region containing fatty tissue.

12. The system of claim 11 wherein determining the threshold intensity value comprises calculating the threshold intensity value using a mean intensity value and a standard deviation of the intensity value.

13. The system of claim 10 wherein the processing unit is configured to:
map coordinates of the corrected thermoacoustic image with coordinates of the ultrasound image.

14. A non-transitory computer-readable medium having stored thereon a computer program comprising computer program code executable by a computer to perform a method comprising:
reconstructing a thermoacoustic absorption image of a region of interest using an assumed speed of sound value;
segmenting the thermoacoustic absorption image into at least one region containing fatty tissue and at least one non fat region containing lean tissue;
creating a speed of sound map by assigning a speed of sound value to each region, the assigned speed of sound value being dependent on an amount of fatty tissue within that region;
correcting aberrations for each region in the segmented thermoacoustic absorption image using a ratio of the assigned speed of sound value to the assumed speed of sound value thereby generating a corrected thermoacoustic image; and
correcting an ultrasound image of the region of interest using the corrected thermoacoustic image and the speed of sound map.

15. A system comprising:
a thermoacoustic imaging system;
an ultrasound imaging system; and
a processing unit configured to:
process thermoacoustic image data received from the thermoacoustic imaging system to generate a thermoacoustic absorption image using an assumed speed of sound value, to identify at least one region containing fatty tissue and at least one region containing lean tissue within the thermoacoustic absorption image, to generate a speed of sound map by assigning a speed of sound value to each region, the assigned speed of sound value being dependent on an amount of fatty tissue within that region and to correct aberrations for each region in the thermoacoustic absorption image using a ratio of the assigned speed of sound value to the assumed speed of sound value thereby generating a corrected thermoacoustic absorption image; and
process ultrasound image data received from the ultrasound imaging system using the speed of sound map and the corrected thermoacoustic absorption image to generate a corrected ultrasound image.

16. The system of claim 15, the processing unit is configured to:
determine a threshold intensity value;
classify pixels within the thermoacoustic absorption image having a threshold above the threshold intensity as being part of the at least one region containing lean tissue; and
classify pixels within the thermoacoustic absorption image having a threshold below the threshold intensity as being part of the at least one region containing fatty tissue.

17. The system of claim 16 wherein determining the threshold intensity value comprises calculating the threshold intensity value using a mean intensity value and a standard deviation of the intensity value.

18. The system of claim 15 wherein the processing unit is configured to map coordinates of the corrected thermoacoustic image to coordinates of the ultrasound image.

19. A method for correcting fat-induced aberrations in ultrasound imaging, the method comprising:

reconstructing a thermoacoustic absorption image of a region of interest using an assumed speed of sound value;

segmenting the thermoacoustic absorption image into at least one fat region of fatty tissue and at least one region of lean tissue;

creating a speed of sound map by assigning a speed of sound value to each region, the assigned speed of sound value being dependent on an amount of fatty tissue within that region;

correcting aberrations for each region in the segmented thermoacoustic absorption image using a ratio of the assigned speed of sound value to the assumed speed of sound value thereby generating a corrected thermoacoustic image; and adjusting parameters of an ultrasound imaging system using the corrected thermoacoustic image and the speed of sound map to correct for fat-induced aberrations.

20. The method of claim 19 wherein the adjusting comprises adjusting a phase of ultrasound signals emitted from at least one transducer array associated with the ultrasound imaging system.

21. The method of claim 20 further comprising:

obtaining ultrasound image data of the region of interest using the ultrasound imaging system at the adjusted phase and reconstructing the ultrasound image using the ultrasound image data.

22. The method of claim 20 wherein the phase of the ultrasound signals is adjusted during beamforming of a high intensity ultrasound beam.

23. The method of claim 20 wherein the ultrasound imaging system is used for at least one of high intensity focused ultrasound and histotripsy.

* * * * *

UNITED STATES PATENT AND TRADEMARK OFFICE
CERTIFICATE OF CORRECTION

PATENT NO. : 10,022,107 B2
APPLICATION NO. : 15/223607
DATED : July 17, 2018
INVENTOR(S) : Michael M. Thornton et al.

It is certified that error appears in the above-identified patent and that said Letters Patent is hereby corrected as shown below:

In the Claims

Column 12, Line 14 reads "non fat region containing" should read --region containing--

Column 13, Line 7 reads "fat region of fatty tissue" should read --region of fatty tissue--

Signed and Sealed this
Twenty-first Day of August, 2018

Andrei Iancu
*Director of the United States Patent and Trademark Office*